US012740800B2

(12) United States Patent
Singh

(10) Patent No.: US 12,740,800 B2
(45) Date of Patent: Sep. 22, 2026

(54) MICROCAVITATION SYSTEM, DEVICE, AND ULTRASONIC PROBE ASSEMBLY FOR GENERATING DIRECTIONAL MICROCAVITATION

(71) Applicant: Bard Peripheral Vascular, Inc., Franklin Lakes, NJ (US)

(72) Inventor: Aseem Singh, Tempe, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 473 days.

(21) Appl. No.: 17/642,784

(22) PCT Filed: Sep. 16, 2019

(86) PCT No.: PCT/US2019/051299
§ 371 (c)(1),
(2) Date: Mar. 14, 2022

(87) PCT Pub. No.: WO2021/054933
PCT Pub. Date: Mar. 25, 2021

(65) Prior Publication Data

US 2022/0395291 A1 Dec. 15, 2022

(51) Int. Cl.
*A61B 17/32* (2006.01)
*A61B 17/3203* (2006.01)

(52) U.S. Cl.
CPC .. *A61B 17/320068* (2013.01); *A61B 17/3203* (2013.01); *A61B 2017/32032* (2013.01)

(58) Field of Classification Search
CPC ........ A61B 17/320068; A61B 17/3203; A61B 2017/32032; A61B 17/32037; A61B 17/22012; A61B 2017/320084
See application file for complete search history.

(56) References Cited

U.S. PATENT DOCUMENTS 5,135,482 A * 8/1992 Neracher ......... A61B 17/32037 606/128
5,163,433 A * 11/1992 Kagawa ........... A61B 17/22012 604/27

(Continued)

FOREIGN PATENT DOCUMENTS

JP H03151954 A 6/1991
JP 2001353165 A 12/2001

(Continued)

OTHER PUBLICATIONS

Japanese Office Action dated Jun. 30, 2023 pertaining to Japanese application No. 2022-516612 filed Mar. 15, 2022, pp. 1-10.

*Primary Examiner* — Mohamed G Gabr
*Assistant Examiner* — Bridget E. Rabaglia
(74) *Attorney, Agent, or Firm* — Dinsmore & Shohl LLP

(57) ABSTRACT

A microcavitation system, device, and ultrasonic probe assembly for generating directional microcavitation includes a cannula and an ultrasonic transmission member. The ultrasonic transmission member has a first end portion and a second end spaced apart from the first end portion. The cannula has a tubular side wall, a cannula lumen, a fluid input port, a proximal end, a distal end, and a distal end portion. The ultrasonic transmission member is located in the cannula lumen. The fluid input port of the cannula is connected in fluid communication with the cannula lumen. The distal end portion of the cannula is configured to define a cavitation generation chamber. The cavitation generation chamber has a distal end wall at the distal end of the cannula that is configured as a sieve to define a plurality of apertures.

18 Claims, 2 Drawing Sheets

(56) References Cited

U.S. PATENT DOCUMENTS

| | | | |
|---|---|---|---|
| 6,096,000 | A | 8/2000 | Tachibana et al. |
| 6,270,471 | B1 * | 8/2001 | Hechel ............. A61B 17/22012 604/35 |
| 6,613,026 | B1 | 9/2003 | Palasis et al. |
| 7,018,354 | B2 * | 3/2006 | Tazi ..................... A61M 1/7411 606/171 |
| 7,115,100 | B2 | 10/2006 | Mcrury et al. |
| 7,892,229 | B2 | 2/2011 | Shadduck et al. |
| 10,016,620 | B2 | 7/2018 | Aljuri et al. |
| 10,166,379 | B2 | 1/2019 | Konofagou et al. |
| 10,183,175 | B2 | 1/2019 | Aljuri et al. |
| 10,321,931 | B2 | 6/2019 | Aljuri |
| 2003/0139041 | A1 * | 7/2003 | LeClair .................. A61B 18/26 438/689 |
| 2013/0253387 | A1 | 9/2013 | Bonutti et al. |
| 2015/0044632 | A1 * | 2/2015 | Bergheim ............ A61C 17/028 433/91 |
| 2018/0206864 | A1 * | 7/2018 | Weitzner ........ A61B 17/320016 |
| 2019/0159792 | A1 | 5/2019 | Panian |

FOREIGN PATENT DOCUMENTS

| | | | |
|---|---|---|---|
| JP | 2014161377 | A | 9/2014 |
| WO | 9858699 | A1 | 12/1998 |
| WO | 0219927 | A1 | 3/2002 |

* cited by examiner

MICROCAVITATION SYSTEM, DEVICE, AND ULTRASONIC PROBE ASSEMBLY FOR GENERATING DIRECTIONAL MICROCAVITATION

CROSS-REFERENCE TO RELATED APPLICATIONS

This application is a U.S. National Phase of International Application No. PCT/US2019/051299, entitled "MICROCAVITATION SYSTEM, DEVICE, AND ULTRASONIC PROBE ASSEMBLY FOR GENERATING DIRECTIONAL MICROCAVITATION" and filed Sep. 16, 2019, which is incorporated herein by reference in its entirety.

TECHNICAL FIELD

The present invention relates to medical ablation, fragmentation, and cutting, and, more particularly, to a microcavitation system, device, and ultrasonic probe assembly for generating directional microcavitation.

BACKGROUND ART

Medical procedures, such as vascular occlusion crossing and/or atherectomy, may utilize ultrasonic energy to cross and/or break up the vascular occlusion through the vibration of a catheter tip engaged with the vascular occlusion. Also, interventional oncology may utilize a mechanical cutting instrument, thermal ablation, or cryogenic techniques, for the removal of a tumor or cancerous lesion.

Acoustic cavitation is the formation and collapse of bubbles in liquid irradiated by intense ultrasound. The speed of the bubble collapse sometimes reaches the sound velocity in the liquid. Accordingly, the bubble collapse becomes a quasi-adiabatic process. Violent bubble collapse during cavitation causes extreme local temperatures, heating/cooling rates and pressures, producing free radicals and giving rise to many chemical (sonochemical) reactions (e.g., oxidation of pollutants, sterilization, polymerization, desulfurization, long-chain molecule degradation, etc.).

What is needed in the art is a microcavitation system, device, and ultrasonic probe assembly for generating directional microcavitation that may be used, for example, in vascular and interventional oncology procedures.

SUMMARY OF INVENTION

The present invention provides a microcavitation system, device, and ultrasonic probe assembly for generating directional microcavitation that may be used, for example, in vascular and interventional oncology procedures.

The invention, in one form, is directed to an ultrasonic probe assembly that includes a cannula and an ultrasonic transmission member. The ultrasonic transmission member has a first end portion and a second end spaced apart from the first end portion. The cannula has a tubular side wall, a cannula lumen, a fluid input port, a proximal end, a distal end, and a distal end portion. The ultrasonic transmission member is located in the cannula lumen. The fluid input port of the cannula is connected in fluid communication with the cannula lumen. The distal end portion of the cannula is configured to define a cavitation generation chamber. The cavitation generation chamber has a distal end wall at the distal end of the cannula that is configured as a sieve to define a plurality of apertures.

The invention, in another form, is directed to an ultrasonic microcavitation device. The ultrasonic microcavitation device includes a handle, an ultrasonic transmission member, and a cannula. The handle contains an ultrasonic transducer. The ultrasonic transmission member has a first end portion and a second end spaced apart from the first end portion. The first end portion of the ultrasonic transmission member is connected to the ultrasonic transducer. The cannula is connected to the handle. The cannula has a tubular side wall, a cannula lumen, a fluid input port, a proximal end, a distal end, and a distal end portion. The ultrasonic transmission member is located in the cannula lumen. The fluid input port of the cannula is connected in fluid communication with the cannula lumen. The distal end portion of the cannula is configured to define a cavitation generation chamber that distally terminates at the distal end of the cannula. The cavitation generation chamber has a distal end wall that is configured as a sieve to define a plurality of apertures for ejecting fluid jetting streams.

The invention, in another form, is directed to a microcavitation system that includes a console, a handle, an ultrasonic transmission member, and a cannula. The console has an ultrasonic signal generator and a fluid source. The handle contains an ultrasonic transducer. The ultrasonic transducer is electrically connected to the ultrasonic signal generator. The ultrasonic transmission member has a first end portion and a second end spaced apart from the first end portion. The first end portion of the ultrasonic transmission member is mechanically connected to the ultrasonic transducer. The cannula is connected to the handle. The cannula has a tubular side wall, a cannula lumen, a fluid input port, a proximal end, a distal end, and a distal end portion that is configured to define a cavitation generation chamber that distally terminates at the distal end. The ultrasonic transmission member is located in the cannula lumen. The fluid input port of the cannula is connected in fluid communication with the fluid source, and the fluid input port is connected in fluid communication with the cannula lumen, wherein the fluid is supplied through the cannula lumen to the cavitation generation chamber. The cavitation generation chamber of the cannula has a distal end wall configured as a sieve to define a plurality of apertures configured to eject fluid jetting streams.

An advantage of the present invention is that directional microcavitation is generated to produce directional fluid jetting streams that are emitted longitudinally from a distal end of the cannula of the ultrasonic probe assembly to provide controlled and directional cutting and/or ablation.

Another advantage is that the microcavitation is directional via the generated cavitation column, thereby providing better tumor margin outcomes than many other tumor removal techniques.

Yet another advantage is that the energy density of the microcavitation is much less destructive to tissue that surrounds the tumor margin, as compared with the harsh environment of RF, thermal, or microwave ablation.

BRIEF DESCRIPTION OF DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DESCRIPTION OF EMBODIMENTS

Figure 1:
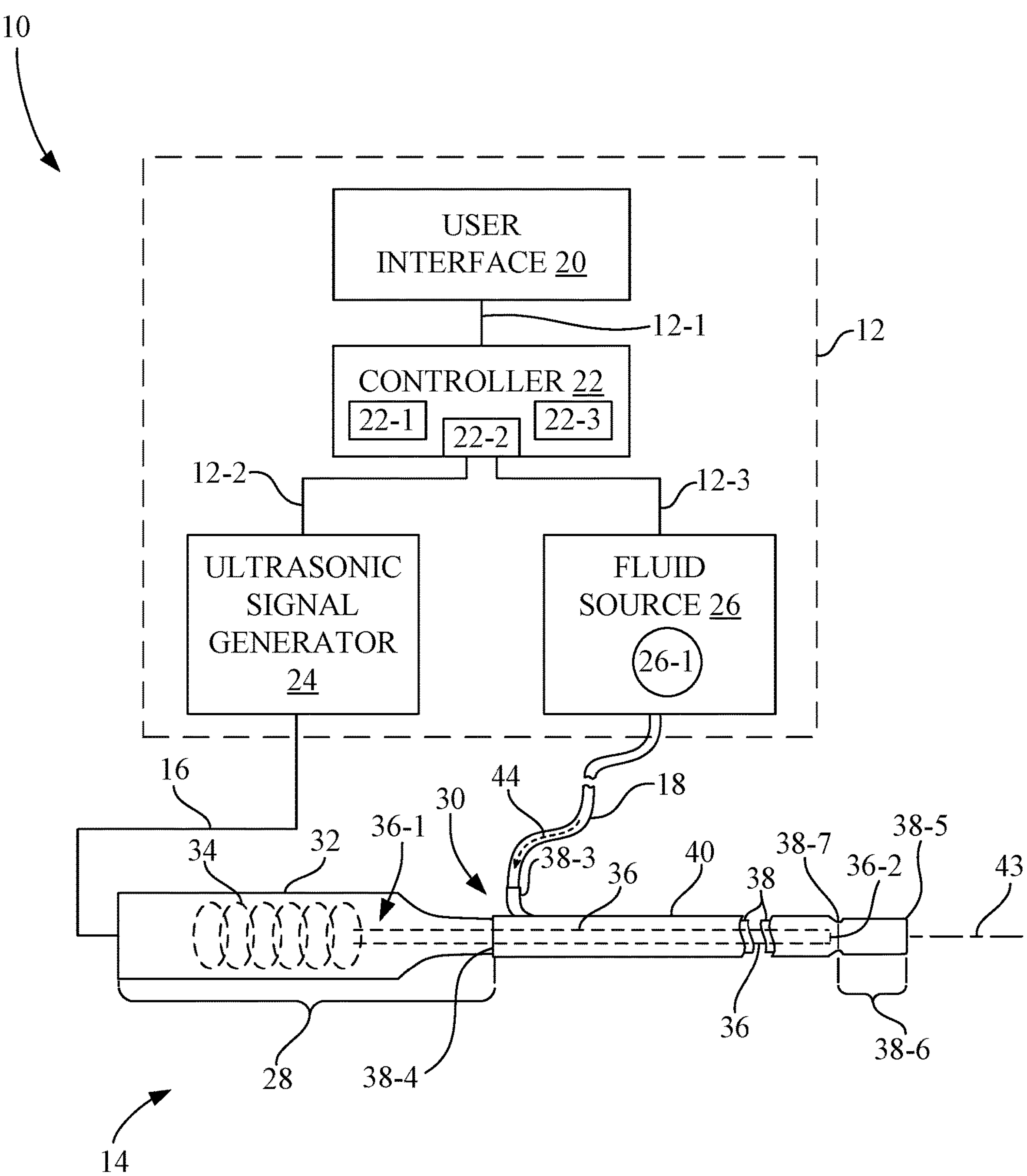
FIG. 1 is a schematic illustration of a microcavitation system in accordance with an embodiment of the present invention, which includes a console and an ultrasonic microcavitation device having an ultrasonic probe assembly having a portion broken away.

Referring now to the drawings, and more particularly to FIG. 1, there is shown a microcavitation system 10 in accordance with an embodiment of the present invention. Microcavitation system 10 generally includes a console 12 and an ultrasonic microcavitation device 14. Ultrasonic microcavitation device 14 may be used, for example, for interventional oncology or vascular procedures.

Console 12 is connected in electrical communication with ultrasonic microcavitation device 14 via an electrical cable 16, e.g., a multi-conductor cable. Console 12 is connected in fluid communication with ultrasonic microcavitation device 14 via a fluid conduit 18, e.g., a flexible tube or hose. Console 12 may include multiple components in a single housing unit or in separate housing units. In the present embodiment, console 12 may include a user interface 20, a controller 22, an ultrasonic signal generator 24, and a fluid source 26.

User interface 20 is connected to controller 22 via an electrical conductor 12-1, e.g., a multi-wire cable or USB, to provide electrical and communication interconnection. Alternatively, user interface 20 may be a wireless link, e.g., Bluetooth, which is communicatively coupled to controller 22. User interface 20 may include, for example, a touchscreen display and associated input and output processing circuitry. Touchscreen display may include, for example, a liquid crystal display (LCD) or a light-emitting diode (LED) display. Alternatively, user interface 20 may be in the form of a laptop computer or tablet. User interface 20 is configured to generate control signals based on user input. For example, a user may operate user interface 20 to provide the control signals to controller 22 to initiate and/or terminate operation of ultrasonic signal generator 24, and/or to selectively start, stop, or control the fluid feed rate of fluid source 26.

Controller 22 is electrically connected and communicatively coupled to user interface 20 via electrical conductor 12-1, e.g., a multi-wire cable or USB. Also, controller 22 is electrically connected and communicatively coupled to ultrasonic signal generator 24 via an electrical conductor 12-2, e.g., a multi-wire cable or USB, and controller 22 is electrically connected and communicatively coupled to fluid source 26 via an electrical conductor 12-3, e.g., a multi-wire cable or USB. Each of electrical conductors 12-2, 12-3 is configured to carry respective output control signals.

Controller 22 includes a processor circuit 22-1, interface circuitry 22-2, and an electronic memory circuit 22-3. Controller 22 executes program instructions to process signals received from user interface 20, executes program instructions to provide output control signals via interface circuit 22-2 to ultrasonic signal generator 24 to control the operation of ultrasonic signal generator 24, and executes program instructions to provide output control signals via interface circuit 22-2 to fluid source 26 to control the operation of fluid source 26.

More particularly, processor circuit 22-1 of controller 22 may include one or more programmable microprocessors and associated circuitry, such as an input/output interface, clock, buffers, memory, etc. Processor circuit 22-1 may be programmed, e.g., through software or firmware stored in electronic memory circuit 22-3, to execute program instructions to process received input data, and to generate and send output data.

Interface circuitry 22-2 includes input and output circuits to facilitate electrical connection and data transfer with user interface 20, ultrasonic signal generator 24, and fluid source 26.

Electronic memory circuit 22-3 is an electronic non-transitory memory having a plurality of data storage locations, as is well known in the art. Electronic memory circuit 22-3 may include one or more of volatile memory circuits, such as random access memory (RAM), and non-volatile memory circuits, such as read only memory (ROM), electronically erasable programmable ROM (EEPROM), NOR flash memory, NAND flash memory, etc. Electronic memory circuit 22-3 may be used, for example, to store program instructions to be executed by processor circuit 22-1 of controller 22 of console 12.

Ultrasonic signal generator 24 is typical of that known in the art, and may be adjustable via user interface 20 and controller 22 to produce an ultrasonic electrical signal in the form of an ultrasonic excitation signal, in a frequency range of 20 kHz-40 kHz, and is adjustable via user interface 20 and controller 22 to produce a variable electrical power output of the ultrasonic excitation signal by adjusting the amplitude of the output voltage and/or current, and/or by adjusting the frequency and/or duty cycle, of the ultrasonic excitation signal.

As shown in FIG. 1, ultrasonic microcavitation device 14 includes a handle 28 and an ultrasonic probe assembly 30. Handle 28 includes a housing 32 that contains an ultrasonic transducer 34 that is mounted internally to housing 32. Housing 32 has an outer shape and size to facilitate being grasped by an operator during a medical procedure, such as for example, an oncological or occlusion related procedure.

Ultrasonic transducer 34 may be, for example, a piezo-electric-type transducer. Ultrasonic transducer 34 of handle 28 is electrically connected to ultrasonic signal generator 24 by electrical cable 16, and is configured to receive and convert the ultrasonic excitation signal generated by ultrasonic signal generator 24 into ultrasonic vibrational energy, which may be in a frequency range corresponding to that of the ultrasonic excitation signal generated by ultrasonic signal generator 24. For example, if the frequency of the ultrasonic excitation signal generated by ultrasonic signal generator 24 and supplied to ultrasonic transducer 34 is 20 kHz, then the vibrational frequency of the output of ultrasonic transducer 34 correspondingly may be 20 kHz.

Ultrasonic probe assembly 30 is mechanically connected to housing 32 of handle 28. Ultrasonic probe assembly 30 generally includes an ultrasonic transmission member 36, a cannula 38, and a cannula sheath 40, wherein cannula sheath 40 is an optional component of ultrasonic probe assembly 30. Also, optionally and alternatively, ultrasonic transmission member 36 may be a component of handle 28.

In a case wherein ultrasonic microcavitation device 14 is intended to be fully disposable, then ultrasonic probe assembly 30 may be permanently attached to handle 28. However, if it is desired that handle 28 of ultrasonic microcavitation device 14 be reusable, then ultrasonic probe assembly 30 may be made to be removably attachable to handle 28, e.g., by a screw coupling or snap connection.

Cannula 38 is a part of ultrasonic probe assembly 30, and thus, is connected to housing 32 of handle 28. In the present embodiment, cannula 38 may be made of a biocompatible metal, such as stainless steel, and is configured to be semi-rigid, i.e., allowing some degree of flexing without permanent deformation. However, it is contemplated that other more flexible and/or non-metal biocompatible materials may be used, depending upon the medical application.

Figure 2:
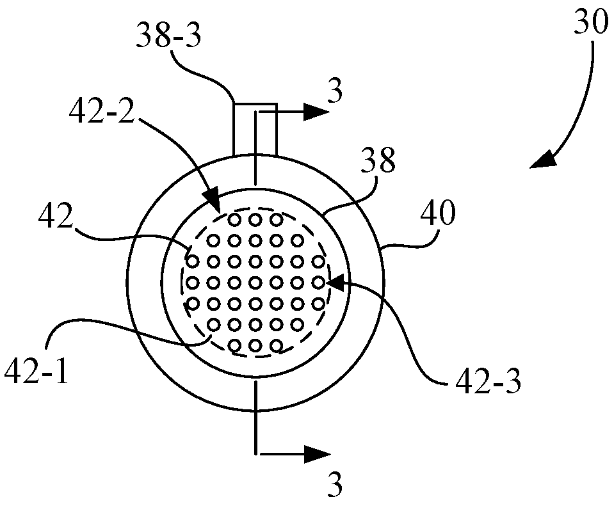
FIG. 2 is an end view of the ultrasonic probe assembly of FIG. 1.
Figure 3:
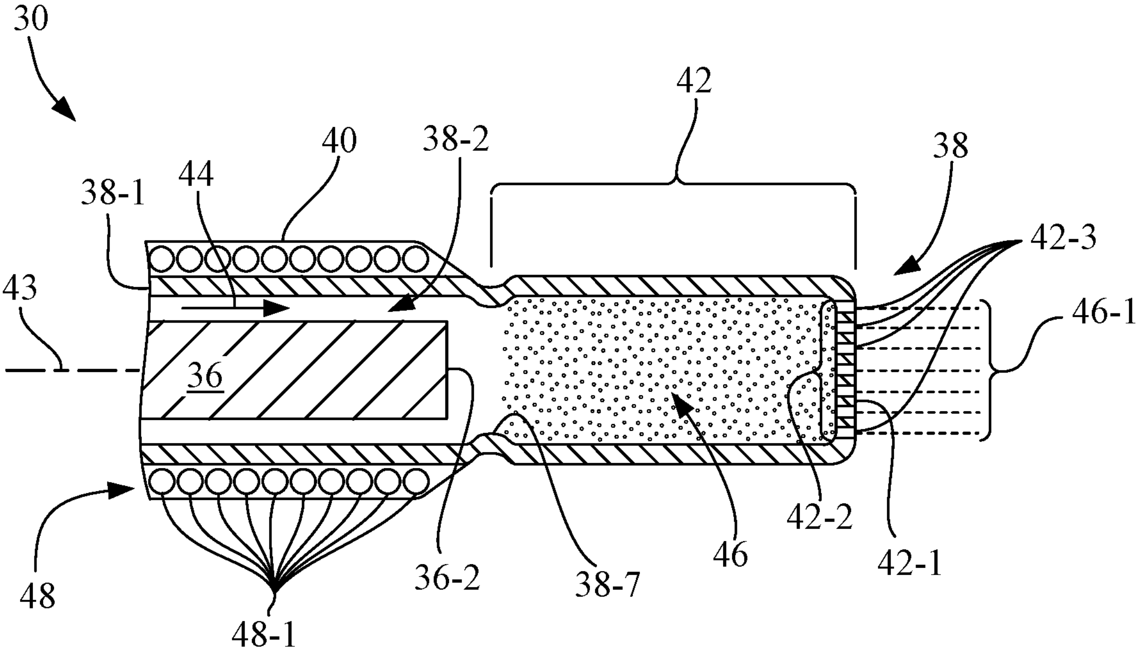
FIG. 3 is a section view of a portion if the ultrasonic probe assembly of FIGS. 1 and 3, taken along line 3-3 of FIG. 2.

Referring also to FIGS. 2 and 3, cannula 38 has a tubular side wall 38-1, a cannula lumen 38-2, a fluid input port 38-3, a proximal end 38-4, a distal end 38-5, and a distal end portion 38-6.

Proximal end 38-4 of cannula 38 is connected to housing 32 of handle 28.

Distal end portion 38-6 is configured to define a cavitation generation chamber 42 that distally terminates at the distal end 38-5. Cavitation generation chamber 42 has a distal end wall 42-1 located at distal end 38-5 of cannula 38. Distal end wall 42-1 of cavitation generation chamber 42 is configured as a sieve 42-2 to define a plurality of apertures 42-3. A longitudinal axis 43 of cannula 38 longitudinally extends through each of cannula lumen 38-2, cavitation generation chamber 42, and sieve 42-2.

Cannula 38 further includes an annular protrusion 38-7 in the cannula lumen 38-2 that extends inwardly from the tubular side wall 38-1. Annular protrusion 38-7 defines a proximal termination end of distal end portion 38-6, and provides a demarcation between cannula lumen 38-2 and cavitation generation chamber 42. Stated differently, annular protrusion 38-7 is configured to define a distal termination end of cannula lumen 38-2 and is configured to define an aft end of the cavitation generation chamber 42. In addition, annular protrusion 38-7 tends to direct the flow stream of fluid entering cavitation generation chamber 42 away from tubular side wall 38-1 of cannula 38.

Fluid input port 38-3 of cannula 38 may be in the form of a Y-connector that provides fluid access to, and is connected in fluid communication with, cannula lumen 38-2. Fluid input port 38-3 is connected by fluid conduit 18 to fluid source 26, such as a saline injector, having a pump 26-1. For example, fluid source 26 may be configured to deliver a fluid 44, e.g., sterile saline, to cannula lumen 38-2 of cannula 38. Fluid 44 may serve to cool ultrasonic transmission member 36 and cannula 38. Moreover, fluid 44 is the fluid used for the generation of microbubble cavitation energy by ultrasonic microcavitation device 14 in cavitation generation chamber 42.

In the present embodiment, cannula lumen 38-2 is an elongate lumen that longitudinally extends within cannula 38 from proximal end 38-4 up to, but not into, cavitation generation chamber 42 of distal end portion 38-6. Cannula lumen 38-2 may be formed as a central lumen, relative to the diameter, of cannula 38. Cannula lumen 38-2 is sized and configured to receive and carry ultrasonic transmission member 36. Also, cannula lumen 38-2 is sized and configured to deliver fluid 44 to cavitation generation chamber 42. However, it is contemplated that cannula lumen 38-2 may alternatively be formed as multiple lumens in cannula 38, wherein a separate fluid lumen may deliver the fluid 44 to cavitation generation chamber 42.

Ultrasonic transmission member 36 may be in the form of an elongate flexible metal wire, e.g., nitinol, which is sometimes also referred to in the art as a core wire. Ultrasonic transmission member 36 is located in, and longitudinally extends within, cannula lumen 38-2 of cannula 38. Ultrasonic transmission member 36 has a first end portion 36-1 and a second end 36-2 spaced apart from the first end portion 36-1. Second end 36-2, i.e., the distal end, of ultrasonic transmission member 36 distally terminates at a location proximal to cavitation generation chamber 42.

First end portion 36-1 of the ultrasonic transmission member 36 is mechanically connected to ultrasonic transducer 34, e.g., by a sonic connector, to receive the vibrational energy from ultrasonic transducer 34 so as to produce a vibrational motion of ultrasonic transmission member 36. Thus, ultrasonic transducer 34 generates vibratory energy at a vibratory energy level corresponding to the electrical energy output level of the ultrasonic excitation signal generated by ultrasonic signal generator 24. The vibrational motion of ultrasonic transmission member 36 may be a combination of longitudinal and transverse vibration.

For example, if the frequency of the ultrasonic excitation signal generated by ultrasonic signal generator 24 and supplied to ultrasonic transducer 34 is 20 kHz, then the vibrational frequency of a longitudinal and/or transverse vibrational motion of distal end portion 38-6 of ultrasonic transmission member 36 correspondingly may be 20 kHz. In this example, each of the longitudinal and/or transverse displacement of second end 36-2 of ultrasonic transmission member 36 may be approximately 100 micrometers when the ultrasonic excitation signal generated by ultrasonic signal generator 24 and supplied to ultrasonic transducer 34 is 20 kHz. The amount of displacement, and the resulting fluid cavitation, may be increased by increasing the ultrasonic excitation signal frequency and/or the electrical power of the ultrasonic excitation signal supplied to ultrasonic transducer 34.

Fluid 44 flows through cannula lumen 38-2 of cannula 38 around and across ultrasonic transmission member 36, and enters cavitation generation chamber 42. Upon activation of ultrasonic transmission member 36, the fluid 44 in cavitation generation chamber 42 of cannula 38 undergoes cavitation to generate within cavitation generation chamber 42 a column of microcavitation bubbles 46 that is directed toward distal end 38-5 of cannula 38. The plurality of apertures 42-3 of sieve 42-2 defined by distal end wall 42-1 of cavitation generation chamber 42 are configured, e.g., sized and shaped, to eject longitudinally directed fluid jetting streams 46-1 along (i.e., on and substantially parallel to) longitudinal axis 43. Due to the fluid dynamics of the generation and collapse of the microcavitation bubbles 46 in cavitation generation chamber 42, the longitudinally directed fluid jetting streams 46-1 are ejected along longitudinal axis 43 through the plurality of apertures 42-3 of sieve 42-2 defined by distal end wall 42-1 of cavitation generation chamber 42. The fluid jetting streams 46-1 emitted from the plurality of apertures 42-3 of sieve 42-2 defined by distal end wall 42-1 of cavitation generation chamber 42 are highly directional micro-jets having a high velocity, e.g., approximately 500 meters per second, and produce high shear forces, thereby being adaptable to a wide range of medical procedures requiring ablation, cutting, or fragmenting of a material substance, such as for example, in performing vascular occlusion crossing, atherectomy, and interventional oncology procedures.

Due to the potential heating of cannula 38 during activation of ultrasonic microcavitation device 14, cannula sheath 40 may be included in ultrasonic microcavitation device 14 to provide additional cooling of cannula 38. In the present embodiment, cannula sheath 40 is positioned over cannula 38 in a region proximal to cavitation generation chamber 42.

In some embodiments, cannula sheath 40 may be permanently attached to cannula 38. Cannula sheath 40 includes a cooling jacket 48 configured as a microtube arrangement 48-1 that surrounds tubular side wall 38-1 of the cannula 38 in a region proximal to cavitation generation chamber 42. Microtube arrangement 48-1 of cooling jacket 48 may be configured, for example, in a crisscross or spiral pattern. Microtube arrangement 48-1 is configured to receive a flow of a cooling fluid, such as sterilized saline, and accordingly, may utilize fluid 44 delivered by fluid source 26 as the cooling fluid. As such, microtube arrangement 48-1 may be connected in fluid communication with fluid source 26.

In operation, a user activates microcavitation system 10 by providing an input at user interface 20. The user input may be, for example, the depression of a pushbutton or a selection made from a displayed menu. User interface 20 then sends an input signal to controller 22.

Controller 22 executes program instructions to process the input signal from user interface 22, and executes program instructions to generate and supply output signals to ultrasonic signal generator 24 and to fluid source 26, which in turn triggers a series of events related to the operation of ultrasonic microcavitation device 14, culminating in the generation of the longitudinally directed fluid jetting streams 46-1 that are emitted from the plurality of apertures 42-3 of sieve 42-2 defined by distal end wall 42-1 of cavitation generation chamber 42 of cannula 38.

In particular, controller 22 produces and outputs a generator control signal to ultrasonic signal generator 24 to cause the ultrasonic signal generator 24 to generate an ultrasonic excitation signal having a predefined electrical energy output level. The ultrasonic excitation signal is supplied to ultrasonic transducer 34, wherein ultrasonic transducer 34 generates vibratory energy at a vibratory energy level corresponding to the electrical energy output level of the ultrasonic excitation signal. Ultrasonic transducer 34, in turn, supplies the vibratory energy to ultrasonic transmission member 36 to activate the ultrasonic transmission member to produce both longitudinal and transverse motion at second end 36-2, i.e., the distal end, of ultrasonic transmission member 36.

Also, controller 22 produces and outputs a fluid control signal to the fluid source 26 to control an amount of flow (e.g., volume per unit time or speed/velocity of a given volume) of fluid 44 generated by the fluid source 26. Fluid source 26 supplies the flow of fluid 44 to the fluid input port 38-3 of the cannula 38, and in turn, fluid 44 travels through cannula lumen 38-2 to cavitation generation chamber 42.

Upon activation of ultrasonic transmission member 36, fluid 44 in cavitation generation chamber 42 of cannula 38 undergoes cavitation to generate within cavitation generation chamber 42 a column of microcavitation bubbles 46 that is directed toward distal end 38-5 of cannula 38. Due to the fluid dynamics of the generation and collapse of the microcavitation bubbles 46 in cavitation generation chamber 42, fluid jetting streams 46-1 are ejected through the plurality of apertures 42-3 of sieve 42-2 defined by distal end wall 42-1 of cavitation generation chamber 42. Accordingly, the directional microcavitation generated in cavitation generation chamber 42 produces directional fluid jetting streams 46-1 that are emitted longitudinally from a distal end 38-5 of cannula 38 of ultrasonic probe assembly 30 to provide controlled and directional cutting and/or ablation by ultrasonic microcavitation device 14 along longitudinal axis 43.

The user may supply further inputs to user interface 20 to adjust an aggressiveness (i.e., velocity and/or pressure) at which the fluid jetting streams 46-1 are emitted, i.e., ejected, through the plurality of apertures 42-3 in distal end wall 42-1 of cavitation generation chamber 42. For example, the user may supply a further input to user interface 20 to select an electrical power output of the ultrasonic excitation signal that is generated by ultrasonic signal generator 24 and supplied to ultrasonic transducer 34 of ultrasonic microcavitation device 14, so as to control the vibratory energy transferred by ultrasonic transmission member 36 to the fluid in cavitation generation chamber 42, so as to control the aggressiveness of the fluid jetting streams 46-1 that are emitted, i.e., ejected, through the plurality of apertures 42-3 in distal end wall 42-1 of cavitation generation chamber 42.

As used herein, the term "approximately", and other words of degree, are relative modifiers intended to indicate permissible variation from the characteristic so modified. It is not intended to be limited to the absolute value or characteristic which it modifies but rather possessing more of the physical or functional characteristic than its opposite, and approaching or approximating such a physical or functional characteristic.

The following items also relate to the invention:

In one form, the invention relates to an ultrasonic probe assembly that includes an ultrasonic transmission member that has a first end portion and a second end spaced apart from the first end portion. The ultrasonic probe assembly further comprises a cannula which has a tubular side wall, a cannula lumen, a fluid input port, a proximal end, a distal end, and a distal end portion. The ultrasonic transmission member is located in the cannula lumen. The fluid input port of the cannula is connected in fluid communication with the cannula lumen. The distal end portion of the cannula is configured to define and/or defines and/or comprises a cavitation generation chamber. The cavitation generation chamber has a distal end wall at the distal end of the cannula that may be configured, in particular may function, as a sieve to define a plurality of apertures.

In any of the embodiments, the cannula has a longitudinal axis that may longitudinally extend through each of the cannula lumen, the cavitation generation chamber, and the sieve.

Some embodiments may include an annular protrusion in the cannula lumen that extends inwardly from the tubular side wall, wherein the annular protrusion may be configured (formed) to define a termination end of the cannula lumen and to define an aft end of the cavitation generation chamber, in particular the annular protrusion defines a termination end of the cannula lumen and an aft end of the cavitation generation chamber.

In any of the embodiments, the ultrasonic transmission member may be located in the cannula lumen of the cannula, and wherein the second end of the ultrasonic transmission member may distally terminate at a location proximal to the cavitation generation chamber.

In any of the embodiments, the cannula may be made of a biocompatible metal.

In any of the embodiments, the ultrasonic probe assembly may optionally include a cannula sheath that has a microtube arrangement that surrounds the tubular side wall of the cannula in a region proximal to the cavitation generation chamber, and/or wherein the microtube arrangement is configured to receive a flow of a cooling fluid.

In the embodiment described immediately above, the cannula sheath may be permanently attached to the cannula.

In another form, the invention relates to an ultrasonic microcavitation device that includes a handle that may contain an ultrasonic transducer. The ultrasonic microcavitation device comprises an ultrasonic transmission member which has a first end portion and a second end spaced apart from the first end portion, wherein the first end portion of the ultrasonic transmission member is connected to the ultrasonic transducer. The ultrasonic microcavitation device further comprises a cannula which may be connected to the handle. The cannula has a tubular side wall, a cannula lumen, a fluid input port, a proximal end, a distal end, and a distal end portion. The ultrasonic transmission member is located in the cannula lumen. The fluid input port of the cannula is connected in fluid communication with the cannula lumen. The distal end portion of the cannula is configured to define and/or defines and/or comprises a cavitation generation chamber that distally terminates at the distal end of the cannula. The cavitation generation chamber has a distal end wall that may be configured, in particular may function, as a sieve to define a plurality of apertures configured to eject fluid jetting streams.

Hence, the ultrasonic microcavitation device may comprise the ultrasonic probe assembly of par. [0051], wherein the ultrasonic microcavitation device further comprises a handle containing an ultrasonic transducer, and the cannula is connected to the handle. The first end portion of the ultrasonic transmission member is connected to the ultrasonic transducer. The plurality of apertures is configured to eject fluid jetting streams.

In any of the embodiments, the cannula has a longitudinal axis that may longitudinally extend through each of the cannula lumen, the cavitation generation chamber, and the sieve.

Some embodiments may include an annular protrusion in the cannula lumen that extends inwardly from the tubular side wall, wherein the annular protrusion may be configured (formed) to define a termination end of the cannula lumen and to define an aft end of the cavitation generation chamber, in particular the annular protrusion defines a termination end of the cannula lumen and an aft end of the cavitation generation chamber.

In any of the embodiments, the ultrasonic transmission member is located in the cannula lumen of the cannula, and wherein the second end of the ultrasonic transmission member distally terminates at a location proximal to the cavitation generation chamber.

In any of the embodiments, the ultrasonic microcavitation device may optionally include a microtube arrangement that surrounds the tubular side wall of the cannula in a region proximal to the cavitation generation chamber, and/or wherein the microtube arrangement is configured to receive a flow of a cooling fluid.

In any of the embodiments, the cannula may be made of a biocompatible metal.

In another form, the invention relates to a microcavitation system that includes a console that may have an ultrasonic signal generator and a fluid source. The microcavitation system comprises a handle which may contain an ultrasonic transducer, wherein the ultrasonic transducer to be electrically connected to the ultrasonic signal generator. An ultrasonic transmission member has a first end portion and a second end spaced apart from the first end portion, wherein the first end portion of the ultrasonic transmission member is mechanically connected to the ultrasonic transducer. A cannula is connected to the handle. The cannula may include a tubular side wall, a cannula lumen, a fluid input port, a proximal end, a distal end, and a distal end portion. The distal end portion is configured to define and/or defines and/or comprises a cavitation generation chamber that distally terminates at the distal end. The ultrasonic transmission member is located in the cannula lumen. The fluid input port of the cannula is connected in fluid communication with the fluid source to receive a flow of a fluid from the fluid source. The fluid input port of the cannula is connected in fluid communication with the cannula lumen, wherein the fluid is to be supplied through the cannula lumen to the cavitation generation chamber, i.e. for supplying fluid through the cannula lumen to the cavitation generation chamber. The cavitation generation chamber of the cannula has a distal end wall that may be configured, in particular may function, as a sieve to define a plurality of apertures configured to eject fluid jetting streams.

Hence, the microcavitation system may comprise the ultrasonic probe assembly of par. [0051] or the ultrasonic microcavitation device of par. [0058], further comprising a console having an ultrasonic signal generator and a fluid source, wherein the ultrasonic transducer is electrically connected to the ultrasonic signal generator. The fluid input port of the cannula may be connected in fluid communication with the fluid source to receive a flow of a fluid from the fluid source; and the fluid input port of the cannula may be connected in fluid communication with the cannula lumen, for supplying fluid through the cannula lumen to the cavitation generation chamber.

In any of the embodiments, the cannula has a longitudinal axis that may longitudinally extend through each of the cannula lumen, the cavitation generation chamber, and the sieve.

Some embodiments may include an annular protrusion in the cannula lumen that extends inwardly from the tubular side wall, wherein the annular protrusion may be configured to define a termination end of the cannula lumen and may be configured to define an aft end of the cavitation generation chamber.

In any of the embodiments, the second end of the ultrasonic transmission member distally terminates at a location proximal to the cavitation generation chamber.

In any of the embodiments, the cannula may be made of a biocompatible metal.

In any of the embodiments, the ultrasonic microcavitation device may optionally include a microtube arrangement that surrounds the tubular side wall of the cannula in a region proximal to the cavitation generation chamber, wherein the microtube arrangement is configured to receive the flow of the fluid from the fluid source to cool the cannula.

According to any embodiment that includes the console, the console may further include a user interface and a controller. The controller may be communicatively coupled to each of the user interface, the ultrasonic signal generator, and the fluid source. The controller may be configured to execute program instructions to: process an input signal from the user interface; provide a first output control signal to the ultrasonic signal generator to cause the ultrasonic signal generator to generate an ultrasonic excitation signal having an electrical energy output level, wherein the ultrasonic excitation signal is to be supplied to the ultrasonic transducer, and to cause the ultrasonic transducer to generate vibratory energy at a vibratory energy level corresponding to the electrical energy output level of the ultrasonic excitation signal; and provide a second output control signal to the fluid source to control an amount of flow of a fluid generated by the fluid source, and to cause the fluid source to supply the flow of fluid to the fluid input port of the cannula.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An ultrasonic probe assembly, comprising:

an ultrasonic transmission member having a first end portion and a second end spaced apart from the first end portion;

a cannula having a tubular side wall, a cannula lumen, an annular protrusion, a fluid input port, a proximal end, a distal end, and a distal end portion; and a fluid source;

a fluid conduit coupling the fluid input port to the fluid source such that the fluid input port is configured to receive a flow of liquid from the fluid source, wherein:

the ultrasonic transmission member is located in the cannula lumen;

the fluid input port of the cannula is connected in fluid communication with the cannula lumen;

the distal end portion of the cannula is configured to define a cavitation generation chamber, the cavitation generation chamber having a distal end wall at the distal end of the cannula, wherein the distal end wall comprises a sieve defining a plurality of apertures configured to eject fluid jetting streams along a longitudinal direction of the cannula, wherein each aperture of the plurality of apertures has an aperture axis that is parallel to a longitudinal axis of the cannula;

the second end of the ultrasonic transmission member distally terminates at a location proximal to the cavitation generation chamber; and the annular protrusion extends inwardly from the tubular side wall into the cannula lumen and is configured to define:

a termination end of the cannula lumen; and an aft end of the cavitation generation chamber.

2. The ultrasonic probe assembly according to claim 1, wherein the longitudinal axis of the cannula extends through each of the cannula lumen, the cavitation generation chamber, and the sieve.

3. The ultrasonic probe assembly according to claim 1, wherein the cannula is made of a biocompatible metal.

4. The ultrasonic probe assembly according to claim 1, further comprising a cannula sheath having a microtube arrangement that surrounds the tubular side wall of the cannula in a region proximal to the cavitation generation chamber, wherein the microtube arrangement is configured to receive a flow of a cooling fluid.

5. The ultrasonic probe assembly according to claim 4, wherein the cannula sheath is attached to the cannula.

6. The ultrasonic probe assembly of claim 1, wherein:

the distal end wall is planar and perpendicular to the longitudinal axis of the cannula; and the plurality of apertures comprises a plurality of linear aperture arrays that are parallel to one another.

7. The ultrasonic probe assembly of claim 1, wherein the plurality of apertures are uniformly sized.

8. The ultrasonic probe assembly of claim 1, wherein the annular protrusion is positioned distally with respect to a termination end of the ultrasonic transmission member.

9. The ultrasonic probe assembly of claim 1, wherein the cavitation generation chamber has a length along the longitudinal axis of the cannula that is greater than a diameter of the cavitation generation chamber.

10. An ultrasonic microcavitation device, comprising:

a handle containing an ultrasonic transducer;

an ultrasonic transmission member having a first end portion and a second end spaced apart from the first end portion, wherein the first end portion of the ultrasonic transmission member is connected to the ultrasonic transducer;

a cannula connected to the handle, the cannula having a tubular side wall, a cannula lumen, an annular protrusion, a fluid input port, a proximal end, a distal end, and a distal end portion;

a fluid source; and a fluid conduit coupling the fluid input port to the fluid source such that the fluid input port is configured to receive a flow of liquid from the fluid source, wherein:

the ultrasonic transmission member is located in the cannula lumen;

the fluid input port of the cannula is connected in fluid communication with the cannula lumen;

the distal end portion of the cannula is configured to define a cavitation generation chamber that distally terminates at the distal end of the cannula, the cavitation generation chamber having a distal end wall comprising a sieve defining a plurality of apertures configured to eject fluid jetting streams along a longitudinal direction of the cannula, wherein each aperture of the plurality of apertures has an aperture axis that is parallel to a longitudinal axis of the cannula;

the second end of the ultrasonic transmission member distally terminates at a location proximal to the cavitation generation chamber; and the annular protrusion extends inwardly from the tubular side wall into the cannula lumen and is configured to define:

a termination end of the cannula lumen; and an aft end of the cavitation generation chamber.

11. The ultrasonic microcavitation device according to claim 10, wherein the longitudinal axis of the cannula extends through each of the cannula lumen, the cavitation generation chamber, and the sieve.

12. The ultrasonic microcavitation device according to claim 10, further comprising a microtube arrangement that surrounds the tubular side wall of the cannula in a region proximal to the cavitation generation chamber, wherein the microtube arrangement is configured to receive a flow of a cooling fluid.

13. The ultrasonic microcavitation device according to claim 10, wherein the cannula is made of a biocompatible metal.

14. A microcavitation system, comprising:

a console having an ultrasonic signal generator and a fluid source;

a handle containing an ultrasonic transducer, wherein the ultrasonic transducer is electrically connected to the ultrasonic signal generator;

an ultrasonic transmission member having a first end portion and a second end spaced apart from the first end portion, wherein the first end portion of the ultrasonic transmission member is mechanically connected to the ultrasonic transducer; and a cannula connected to the handle, the cannula having a tubular side wall, a cannula lumen, an annular protrusion, a fluid input port, a proximal end, a distal end, and a distal end portion that is configured to define a cavitation generation chamber that distally terminates at the distal end, wherein:

the ultrasonic transmission member is located in the cannula lumen;

the fluid input port of the cannula is connected in fluid communication with the fluid source to receive a flow of a fluid from the fluid source;

the fluid input port of the cannula is connected in fluid communication with the cannula lumen, wherein the fluid is supplied through the cannula lumen to the cavitation generation chamber;

the cavitation generation chamber of the cannula has a distal end wall comprising a sieve defining a plurality of apertures configured to eject fluid jetting streams along a longitudinal direction of the cannula, wherein each aperture of the plurality of apertures has an aperture axis that is parallel to a longitudinal axis of the cannula;

the second end of the ultrasonic transmission member distally terminates at a location proximal to the cavitation generation chamber; and the annular protrusion extends inwardly from the tubular side wall into the cannula lumen and is configured to define:

a termination end of the cannula lumen; and an aft end of the cavitation generation chamber.

15. The microcavitation system according to claim 14, wherein the longitudinal axis of the cannula extends through each of the cannula lumen, the cavitation generation chamber, and the sieve.

16. The microcavitation system according to claim 14, wherein the cannula is made of a biocompatible metal.

17. The microcavitation system according to claim 14, further comprising a microtube arrangement that surrounds the tubular side wall of the cannula in a region proximal to the cavitation generation chamber, wherein the microtube arrangement is configured to receive the flow of the fluid from the fluid source to cool the cannula.

18. The microcavitation system according to claim 14, wherein the console further includes a user interface and a controller, the controller being communicatively coupled to each of the user interface, the ultrasonic signal generator, and the fluid source, the controller configured to execute program instructions to:

process an input signal from the user interface;

provide a first output control signal to the ultrasonic signal generator to cause the ultrasonic signal generator to generate an ultrasonic excitation signal having an electrical energy output level, the ultrasonic excitation signal being supplied to the ultrasonic transducer, wherein the ultrasonic transducer generates vibratory energy at a vibratory energy level corresponding to the electrical energy output level of the ultrasonic excitation signal; and provide a second output control signal to the fluid source to control an amount of flow of a fluid generated by the fluid source, the fluid source supplying the flow of fluid to the fluid input port of the cannula.

* * * * *